(12) United States Patent
Inoue et al.

(10) Patent No.: US 8,877,443 B2
(45) Date of Patent: Nov. 4, 2014

(54) METHOD AND KIT FOR EVALUATION OF PREDISPOSITION TO DEVELOPMENT OF OBESITY, ANTI-OBESITY AGENT AND METHOD FOR SCREENING THEREOF, NON-HUMAN ANIMAL, ADIPOSE TISSUE, ADIPOCYTE, METHOD FOR PRODUCTION OF TRANSGENIC MOUSE, ANTIGEN, AND ANTIBODY

(75) Inventors: Satoshi Inoue, Tokyo (JP); Tomohiko Urano, Tokyo (JP); Yasuyoshi Ouchi, Tokyo (JP); Masataka Shiraki, Nagano (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 13/320,674

(22) PCT Filed: May 17, 2010

(86) PCT No.: PCT/JP2010/003314
§ 371 (c)(1),
(2), (4) Date: Nov. 15, 2011

(87) PCT Pub. No.: WO2010/131491
PCT Pub. Date: Nov. 18, 2010

(65) Prior Publication Data
US 2012/0060231 A1 Mar. 8, 2012

(30) Foreign Application Priority Data

May 15, 2009 (JP) ................. 2009-119012

(51) Int. Cl.
| | | |
|---|---|---|
| C12Q 1/68 | (2006.01) | |
| C07H 21/04 | (2006.01) | |
| A61K 31/496 | (2006.01) | |
| A61K 31/198 | (2006.01) | |
| C07K 16/18 | (2006.01) | |
| G01N 33/68 | (2006.01) | |
| A61K 38/04 | (2006.01) | |
| A61K 31/5377 | (2006.01) | |
| C07K 14/705 | (2006.01) | |
| A61K 31/519 | (2006.01) | |
| C12N 15/85 | (2006.01) | |
| A61K 45/06 | (2006.01) | |

(52) U.S. Cl.
CPC ............ A61K 31/198 (2013.01); A61K 31/496 (2013.01); *C07K 2317/34* (2013.01); *C12Q 2600/136* (2013.01); *G01B 2800/044* (2013.01); *C12Q 2600/156* (2013.01); C07K 16/18 (2013.01); G01N 33/6893 (2013.01); A61K 38/04 (2013.01); A61K 31/5377 (2013.01); *A01K 2217/052* (2013.01); *G01N 2500/00* (2013.01); C07K 14/705 (2013.01); *A01K 2267/0362* (2013.01); *A01K 2217/075* (2013.01); *C12Q 2600/172* (2013.01); A61K
*31/519* (2013.01); C12Q 1/6883 (2013.01); C12N 15/8509 (2013.01); A61K 45/06 (2013.01)
USPC ........ 435/6.11; 435/6.12; 435/91.1; 536/23.1

(58) Field of Classification Search
None
See application file for complete search history.

(56) References Cited

U.S. PATENT DOCUMENTS

2003/0092019 A1* 5/2003 Meyer et al. ................. 435/6

FOREIGN PATENT DOCUMENTS

| | | | | |
|---|---|---|---|---|
| JP | 2006-509519 | 3/2006 | | |
| JP | 2006-524044 | 10/2006 | | |
| JP | 2007-298045 | 11/2007 | | |
| JP | 2008-536474 | 9/2008 | | |
| JP | 2008-546380 | 12/2008 | | |
| WO | WO-2004/055180 | 7/2004 | | |
| WO | WO-2004/094659 | 11/2004 | | |
| WO | WO-2006/063332 | 6/2006 | | |
| WO | WO-2006/134154 | 12/2006 | | |
| WO | WO 2009/063843 | * 5/2009 | ............ | C01N 33/15 |
| WO | WO-2009/063843 | 5/2009 | | |

OTHER PUBLICATIONS

SLC25A24 protein sequence, printout from www.ncbi.nlm.nih.gov/protein/NP_037518.3, Dated Oct. 11, 2012. pp. 1-8. Also see SLC25A24 nucleic acid sequence.*
SLC25A24 nucleic acid sequence. Printout from www.ncbi.nlm.nih.gov/nuccore/NC_000001.10?report=genebank&from=108677344&to=1087429808&strand=true. dated Oct. 11, 2012. pp. 1-20.*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*

(Continued)

*Primary Examiner* — Jeanine A Goldberg
(74) *Attorney, Agent, or Firm* — Edwards Wildman Palmer LLP; David G. Conlin; Christopher R. Cowles

(57) ABSTRACT

It is an object of the present invention to provide a method of evaluating whether or not a subject has a predisposition to obesity or an obesity-related condition or disease, a kit for conducting the method, an anti-obesity drug having an effect of preventing or treating obesity or an obesity-related condition or disease, a method of screening the anti-obesity drug, a non-human animal having a deficiency in the gene associated with obesity, and an adipose tissue or adipocyte of the animal. The method of evaluating a predisposition to obesity of the present invention is a method of evaluating whether or not a subject has a predisposition to obesity or an obesity-related condition or disease. The method includes the step of detecting a copy number variation (CNV) in intron 1 of SLC25A24 gene or a gene polymorphism having a linkage disequilibrium relationship with the CNV in a sample containing a human gene of the subject. If the CNV in intron 1 of the SLC25A24 gene is 0, the subject may be evaluated to have a predisposition to obesity or an obesity-related condition or disease.

1 Claim, 17 Drawing Sheets

(56) References Cited

OTHER PUBLICATIONS

Lucentini (The Scientist; 2004, vol. 24, p. 20).*
Database of Genomic Variants, Chromosome 1p13.3, 108,600,000-109100000 accessed Apr. 2013.*
Redon et al (Nature, vol. 444, pp. 444-454, 2006).*
Smyth et al. (Diabetes, vol. 57, pp. 1730, Jun. 2008).*
Nastiuk et al (Prostates, vol. 40, No. 3, pp. 172-177, 1999).*
Database of Genomic Variants, Chromosome 1p13.3, 108,530,000-108535800 accessed Jan. 2014.*
Abnova, "SLC25A24 purfied MaxPab mouse polyclonal antibody (B01P)", Catalog #:H00029957, pp. 1-3.
NCBI, "dbSNP Short Genetic Variatons", XP007921128, pp. 1-3.
Smyth et al., "PTPN22 Trp$^{620}$ Explains the Association of Chromosome 1p13 With Type 1 Diabetes and Shows a Statistical Interaction With HLA Class II Genotypes", Diabetes, vol. 57, Jun. 2008, XP008155600, pp. 1730-1737.
GeneTex, "SLC25A24 antibody, Internal", Catalog No. GTX46817, Oct. 10, 2012, pp. 1-2.
Keller et al., "A gene expression network model of type 2 diabetes links cell cycle regulation in islets with diabetes susceptibility", Genome Research 2008 18: pp. 706-716.
Redon et al., Global variation in number in the human genome, Nature, vol. 444, Nov. 23, 2006, pp. 444-454.
LSBio, "SLC25A24 Rabbit anti-Human Polyclonal (Internal) Antibody—LS-C80623—LSBio", XP007921135, pp. 1-2.
GenPept, solute carrier family 25 member 24 isoform 1 [*Homo sapiens*], NCBI Reference Sequence: NP_037518.2, pp. 1-2.
Supplemental European Search Report mailed Oct. 26, 2012 in corresponding European Patent Application No. 10774750.3.
del Arco et al., Identification of a Novel Human Subfamily of Mitochondrial Carriers with Calcium-binding Domains*, The Journal of Biological Chemistry, vol. 279, No. 23, Issue of Jun. 4, 2004, pp. 24701-24713.

* cited by examiner (a)

| Probe Set ID | Gene Symbol | mRNA Accession |
|---|---|---|
| 10500565 | Hsd3b1 | NM_008293 |
| 10429538 | Cyp11b1 | NM_001033229 |
| 10585794 | Cyp11a1 | NM_019779 |
| 10587616 | Prss35 | NM_178738 |
| 10452854 | Srd5a2 | NM_053188 |
| 10450272 | Cyp21a1 | NM_009995 |
| 10500559 | Hsd3b6 | NM_013821 |
| 10571054 | Star | NM_011485 |
| 10589773 | Lba1 | BC086653 |
| 10476355 | Chgb | NM_007694 |
| 10537169 | Akr1b7 | NM_009731 |
| 10429295 | Kcnk9 | NM_001033876 |
| 10470412 | Th | NM_138942 |
| 10526169 | Dbh | NM_181045 |
| 10429547 | Caln1 | NM_009991 |
| 10569370 | Cyp11b2 | NM_009377 |
| 10500570 | Hao3 | NM_019545 |
| 10567879 | Atp2a1 | NM_007504 |
| 10380891 | Pnmt | NM_008890 |
| 10377117 | Myh4 | NM_010855 |
| 10397882 | Chga | NM_007693 |
| 10355960 | Scg2 | NM_009129 |
| 10346878 | Zdbf2 | ENSMUST00000114132 |
| 10548899 | Rerg | NM_181988 |
| 10602756 | Smpx | NM_025357 |
| 10601701 | Tmem35 | NM_026239 |
| 10399407 | Vsnl1 | NM_012038 |
| 10593756 | Chrna3 | NM_145129 |
| 10349773 | Klhdc8a | NM_144810 |

FIG. 13

| Probe Set ID | Gene Symbol | mRNA Accession |
|---|---|---|
| 10499899 | Sprr1a | NM_009264 |
| 10493850 | Sprr2a | NM_011468 |
| 10349648 | Ctse | NM_007799 |
| 10432785 | Krt5 | NM_027011 |
| 10441254 | Tmprss2 | NM_015775 |
| 10424662 | Psca | NM_028216 |
| 10562050 | Upk1a | NM_026815 |
| 10603059 | Tmem27 | NM_020626 |
| 10437205 | Pcp4 | NM_008791 |
| 10493856 | Sprr2a | ENSMUST00000090872 |
| 10493858 | Sprr2a | ENSMUST00000090872 |
| 10428176 | Snx31 | NM_025712 |
| 10548692 | Kap | NM_010594 |
| 10390850 | Krt20 | NM_023256 |
| 10499904 | Ivl | NM_008412 |
| 10531073 | Ugt2b38 | NM_133894 |
| 10514532 | Cyp2j5 | NM_010007 |
| 10410007 | Fbp1 | NM_019395 |
| 10440647 | Cldn8 | NM_018778 |
| 10461758 | Keg1 | BC010803 |
| 10499412 | Rab25 | NM_016899 |
| 10583809 | Cnn1 | NM_009922 |
| 10361887 | Perp | NM_022032 |
| 10404402 | Foxq1 | NM_008239 |
| 10349108 | Serpinb5 | NM_009257 |
| 10545168 | Tacstd2 | NM_020047 |
| 10575052 | Cdh1 | NM_009864 |
| 10428960 | Gsdmc3 | NM_183194 |
| 10556718 | Acsm2 | NM_146197 |
| 10576049 | Foxf1a | ENSMUST00000098351 |
| 10545707 | Actg2 | NM_009610 |

(a)
* P=0.043, COMPARISON BETWEEN Wt MICE AND SLC25A24 TRANSGENIC MICE LINE 14

(b)
* P=0.0070, COMPARISON BETWEEN Wt MICE AND SLC25A24 TRANSGENIC MICE LINE 14

METHOD AND KIT FOR EVALUATION OF PREDISPOSITION TO DEVELOPMENT OF OBESITY, ANTI-OBESITY AGENT AND METHOD FOR SCREENING THEREOF, NON-HUMAN ANIMAL, ADIPOSE TISSUE, ADIPOCYTE, METHOD FOR PRODUCTION OF TRANSGENIC MOUSE, ANTIGEN, AND ANTIBODY

TECHNICAL FIELD

The present invention relates to a method of evaluating whether or not a subject has a predisposition to obesity or an obesity-related condition or disease, a kit for conducting the method, an anti-obesity drug having an effect of preventing or treating obesity or an obesity-related condition or disease, a method of screening the anti-obesity drug, a non-human animal having a deficiency in a gene associated with obesity or stably overexpressing the gene, an adipose tissue or adipocyte of the animal, a method of producing a transgenic mouse of a gene associated with obesity, an antigen, and an antibody.

BACKGROUND ART

Obesity causes various diseases including metabolic syndromes to decrease the ADL and QOL of people. Obesity is a condition that the body fat mass is excessively increased. The number of obesity population is steadily increasing with recent changes in dietary habits, and medical expenses for complications accompanied by obesity are also increasing.

This suggests that early treatment is important, but a marker for predicting early stage of obesity has not been obtained yet.

There are methods using gene polymorphisms for diagnosing obesity. Examples of existing technology relating to such methods include the following Patent Literatures 1 to 4.

Patent Literature 1 discloses detection of a gene encoding a protein selected from PAPPA, PAM, pf20, DNAH11, PKD1, KCNMA1, PKHD1, NRXN3, EPHA7, ROS1, FKSG87, C3orf6, TOX, DLG2, MDS1, FABP2, EFA6R, FLJ20125, C1orf10, CHL1, BICD1, KREMEN1, ADARB2, A2BP1, MGC4309, PIGR, PCSK7, and HSF2 or of a polymorphism closely linked to the gene;

Patent Literature 2 discloses detection of a polymorphism of frizzled-related protein (FRZB) gene;

Patent Literature 3 discloses detection of a polymorphism in a 5' region of gad2 gene; and Patent Literature 4 discloses detection of an SNP of ENPP1.

However, these existing technologies have not been applied to practical use.

The present inventors have performed comprehensive analysis of about fifty thousand single nucleotide polymorphisms (SNPs) present in human genes and investigated correlation with the body fat mass, as disclosed in Patent Literature 5. As a result, it was found that, for example, an SNP (rs491785) in intron 2 of SLC25A24 gene causes a predisposition to obesity.

CITATION LIST

Patent Literature

Patent Literature 1: Japanese Unexamined Patent Application Publication (Translation of PCT Application) No. 2008-536474, "Markers for metabolic syndrome, obesity, and insulin resistance"

Patent Literature 2: Japanese Unexamined Patent Application Publication (Translation of PCT Application) No. 2006-524044, "Associations of polymorphisms in FRZB gene with obesity and osteoporosis"

Patent Literature 3: Japanese Unexamined Patent Application Publication (Translation of PCT Application) No. 2006-509519, "Method of diagnosis of obesity"

Patent Literature 4: Japanese Unexamined Patent Application Publication (Translation of PCT Application) No. 2008-546380, "ENPP1 (PC-1) gene haplotype associated with risk of obesity and type 2 diabetes mellitus and their applications"

Patent Literature 5: Japanese Patent Application No. 2007-298045, "Method of judging risk of developing obesity based on gene polymorphism associated with human body fat mass".

SUMMARY OF INVENTION

Technical Problem

Accordingly, as effective measures extended from the findings disclosed in Patent Literature 5, it is an object of the present invention to provide a method of evaluating whether or not a subject has a predisposition to obesity or an obesity-related condition or disease, a kit for conducting the method, an anti-obesity drug having an effect of preventing or treating obesity or an obesity-related condition or disease, a method of screening the anti-obesity drug, a non-human animal having a deficiency in the gene associated with obesity, and an adipose tissue or adipocyte of the animal.

Solution to Problem

The method of evaluating a predisposition to obesity of the present invention is a method of evaluating whether or not a subject has a predisposition to obesity or an obesity-related condition or disease. The method includes the step of detecting a copy number variation (CNV) in intron 1 of SLC25A24 gene or a gene polymorphism having a linkage disequilibrium relationship with the CNV in a sample containing a human gene of the subject.

If the CNV in intron 1 of the SLC25A24 gene is 0, the subject may be evaluated to have a predisposition to obesity or an obesity-related condition or disease.

The gene polymorphism may be detected by any of a BAC array CGH method, a FISH method, an RFLP method, a PCR-SSCP method, an allele-specific oligonucleotide hybridization method, a direct sequencing method, a TaqMan PCR method, an invader method, an MALDI-TOF/MS method, a molecular beacon method, an RCA method, a UCAN method, and a nucleic acid hybridization method using a DNA chip or a DNA microarray.

The subject may be a Japanese.

The present invention may be provided as an evaluation kit, and the kit for evaluating a predisposition to obesity according to the present invention is a kit for evaluating whether or not a subject has a predisposition to obesity or an obesity-related condition or disease, and the kit includes measures for detecting a CNV in intron 1 of SLC25A24 gene or a gene polymorphism having a linkage disequilibrium relationship with the CNV in a sample containing a human gene of the subject.

Furthermore, the method of screening an anti-obesity drug according to the present invention includes the steps of evaluating whether or not each test substance can suppress or regulate the expression of SLC25A24 gene or can inhibit or regulate the activity thereof; and selecting a test substance that can suppress or regulate the expression of the SLC25A24 gene or can inhibit or regulate the activity thereof and thereby prevents or treats obesity or an obesity-related condition or disease, as an active substance for preventing or treating obesity or an obesity-related condition or disease.

Furthermore, the method may include the steps of administering the test substances to non-human animals; measuring the degrees of obesity of the non-human animals administered with the test substances; and selecting a test substance that reduces the degree of obesity, as an active substance.

In addition, the anti-obesity drug of the present invention is an anti-obesity drug having an effect of preventing or treating obesity or an obesity-related condition or disease and contains an agent that suppresses or regulates the expression of the SLC25A24 gene or inhibits or regulates the activity thereof and has an effect of suppressing differentiation of adipocytes.

Furthermore, the non-human animal of the present invention has a deficiency in the SLC25A24 gene.

The non-human animal of the present invention overexpresses or stably expresses the SLC25A24 gene.

The non-human animal of the present invention may be in an anti-obesity state where differentiation of adipocytes is suppressed.

The present invention may be provided as an adipose tissue or an adipocyte derived from such a non-human animal.

Furthermore, the method of producing a transgenic mouse according to the present invention is a method of producing a transgenic mouse showing suppression in body weight gain compared with a wild-type mouse, wherein gene induction is performed using a plasmid vector containing the SLC25A24 gene to overexpress or stably express the SLC25A24 gene.

Furthermore, the anti-SLC25A24 protein antibody of the present invention is an antibody specifically reacting with an SLC25A24 protein, wherein the antibody is produced using an antigen containing EWRDYFLFNPVTDIEE of an amino acid sequence constituting the SLC25A24 protein, as an epitope.

The antigen for producing an anti-SLC25A24 protein antibody of the present invention is an antigen that is used for producing an antibody that specifically reacts with the SLC25A24 protein and contains EWRDYFLFNPVTDIEE of an amino acid sequence constituting the SLC25A24 protein, as an epitope.

Advantageous Effects of Invention

The method and the kit for evaluating a predisposition to obesity according to the present invention effectively evaluate whether or not a subject has a predisposition to obesity or an obesity-related condition or disease and thereby contribute to prevention and treatment.

The anti-obesity drug according to the present invention contains an agent that suppresses or regulates the expression of the SLC25A24 gene or inhibits or regulates the activity thereof and thereby suppresses differentiation of adipocytes. Therefore, the drug can prevent or treat obesity or an obesity-related condition or disease without causing unfavorable other effects.

Accordingly, the drug is also effective for prevention or treatment of, for example, diabetes mellitus, hyperlipidemia, hypertension, hyperinsulinemia, arteriosclerosis, or polycystic ovary syndrome.

The non-human animal according to the present invention is useful as a model animal in an anti-obesity state or a model animal in an obesity state.

The adipose tissue or the adipocyte according to the present invention is useful as a model tissue or cell.

The method of producing a transgenic mouse according to the present invention is useful as a method of producing a model animal.

The antigen or the antibody according to the present invention is useful for confirming a deficiency of the SLC25A24 protein.

BRIEF DESCRIPTION OF DRAWINGS

FIG. 12 is a list of genes that showed increased expression levels in knockout mice.

FIG. 13 is a list of genes that showed decreased expression levels in knockout mice.

DESCRIPTION OF EMBODIMENTS

The present inventors have also found a correlation between CNV in intron 1 of the SLC25A24 gene and body fat mass as an extension of the findings disclosed in Patent Literature 5. Furthermore, the inventors have confirmed a linkage disequilibrium relationship between CNV and SNP. Then, the inventors have conducted demonstration experiments using mice to arrive at the present invention.

The present invention will be described with reference to examples and the demonstration experiments supporting the present invention below. Embodiments of the present invention are not limited to examples shown below, and conventionally known technologies, such as those disclosed in Patent Literature 5, can be appropriately employed.

Figure 1:
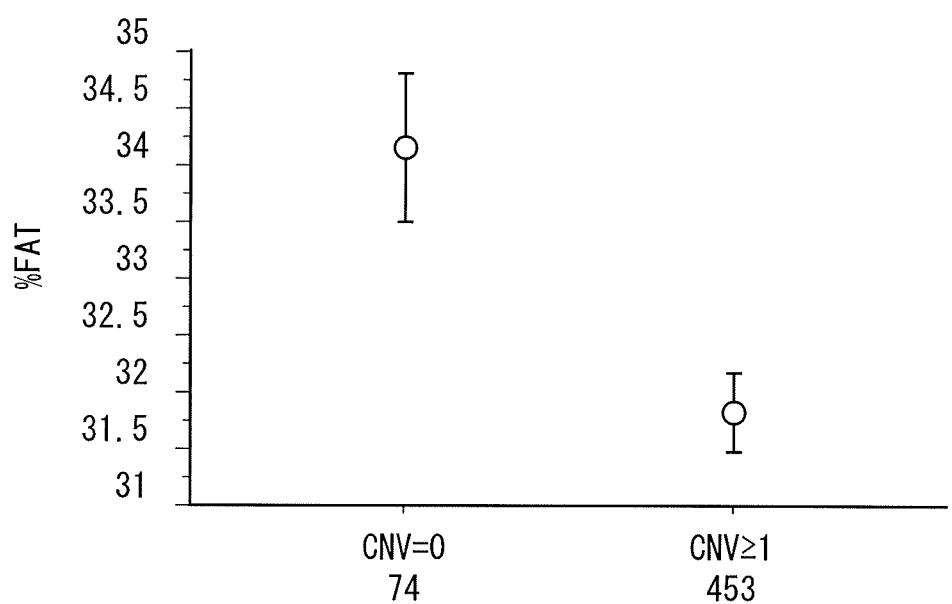
FIG. 1 is a graph showing a relationship between CNV in intron 1 of the SLC25A24 gene and body fat mass.

FIG. 1 is a graph showing a relationship between CNV in intron 1 of the SLC25A24 gene and body fat mass.

Body fat percentages (% FAT) of 527 postmenopausal women were measured by a DEXA method. DNA was collected from peripheral blood of each subject, and the copy number of CNV present in intron 1 (chromosome 1: 108534690-108535300) of the SLC25A24 gene was judged.

In the detection of CNV, the SLC25A24-RNaseP deltaCt value was calculated by qPCR analysis of 5 ng of a target gDNA using TaqMan probe and primer (FAM label) for intron 1 of the SLC25A24 gene and RNaseP (VIC label, ABI: 4316844) as a reference gene, and the deltaCt value of 5 ng of reference gDNA HapMap NA19000 was similarly calculated. Then, the deltaCt value was calculated by subtracting the reference gDNA deltaCt value from the target gDNA deltaCt value. The copy number was judged by principal component analysis by a Gaussian mixture model using the log2 converted value of the deltaCt value of the target sample.

The results were that 74 subjects were CNV=0, 94 subjects were CNV=1, 252 subjects were CNV=2, and 30 subjects were CNV=4. The % FAT of the subjects of CNV=0 and the % FAT of the subjects of CNV=1 or more were verified by unpaired t-test to reveal that there was a statistically significant difference between the % FAT values of the two groups and that the body fat masses of the subjects of CNV=0 were large.

Thus, it is possible to evaluate whether or not a subject has a predisposition to obesity or an obesity-related condition or disease by detecting a CNV in intron 1 of the SLC25A24 gene or a gene polymorphism having a linkage disequilibrium relationship with the CNV in a sample containing a human gene of the subject. This may be provided as a kit, such as a DNA chip, for evaluating a predisposition to obesity.

The detection of a gene polymorphism having a linkage disequilibrium relationship with this CNV may be used for evaluating whether or not a subject has a predisposition to obesity or an obesity-related condition or disease.

Identification of the linkage disequilibrium relationship between the CNV and the SNP may be performed by determining the frequency of each allele of gene polymorphisms genotyped between different CNV groups. For example, first, gene polymorphisms are genotyped. Subsequently, the frequency of each allele of the genotyped gene polymorphisms was subjected to a chi-square test between a group of CNV=0 and a group of CNV=1 or more. The statistically significant gene polymorphism ($P<0.05$) can be defined as a gene polymorphism having a linkage disequilibrium relationship with the CNV.

In the case of SNP, D' and r2 are calculated from genotyping results, and those having a value near 1 can be defined to be linkage disequilibrium.

The CNV refers to a genomic region where the number of copies per cell differs in each individual in a specific population. As other polymorphisms in number of genomic DNA, for example, SNP, VNTR, and microsatellite polymorphism are known.

In the CNV, a case of a number of copies relatively larger than that of a control is referred to as a duplication, and a case of a number of copies relatively smaller than that of a control is referred to as a deletion. In general, the cell of, for example, a human has 2 copies of a gene, one is from the paternal side and the other is from the maternal side. However, some individuals have one copy of a gene or three or more copies of a gene per cell. Such a duplication or a deletion of the gene is frequently observed in the genome of a human expressing a normal phenotype, and it is suggested a possibility of that the CNV is widely associated with the differences in phenotype of a human, including susceptibility to diseases and susceptibility to drugs.

Furthermore, some of genes have an allele showing the normal function, an allele accelerating or suppressing the function, or an allele completely losing the function, and not only the gene level but also a change in the number of copies of a specific allele affects the phenotype in some cases.

In the method of detecting a CNV and a gene polymorphism having a linkage disequilibrium relationship with the CNV, human blood or tissue is used as a sample, and, for example, a BAC array CGH method, a FISH method, an RFLP method, a PCR-SSCP method, an allele-specific oligonucleotide hybridization method, a direct sequencing method, a TaqMan PCR method, an invader method, an MALDI-TOF/MS method, a molecular beacon method, an RCA method, a UCAN method, or a nucleic acid hybridization method using a DNA chip or a DNA microarray can be used.

For example, the BAC array CGH method is a comparative genomic hybridization method using an array prepared by spotting BAC clones composed of DNA fragments produced by Macrogen's KoGENOME Project on a glass slide and is a method of detecting a CNV by labeling a DNA to be tested and a DNA derived from a normal cell with different fluorescence dyes, respectively, and comparing the fluorescence intensities.

As the BAC clone-spotted array, a commercially available one also can be used. For example, MAC Array (registered trademark) available from Macrogen Corp. and SpectralChip (registered trademark) available from Spectral Genomics, Inc. are known.

The DNA that is subjected to a reaction with the BAC clones is labeled by, for example, a random prime method. A solution of the labeled DNA is washed with sodium acetate or ethanol for removing the labeling material and other substances that have not been taken in by the DNA. The purified labeled DNA is dissolved in a hybridization solution. The DNA is thermally denatured by heating the solution in a water bath, and the repeating sequence is blocked by leaving the solution to stand in an incubator.

The array slide after hybridization and washing can provide images of fluorescence from the test DNA and the control DNA using a quantitative detection apparatus such as a laser scanner or a CCD camera.

In the FISH method, a probe having a DNA sequence that can hybridize to a genomic region to be investigated of a chromosome specimen is labeled with a fluorescent material, the labeled probe is allowed to hybridize to the genomic region of the chromosome, and the fluorescent signals obtained thereby is counted under a fluorescence microscope.

Figure 2:
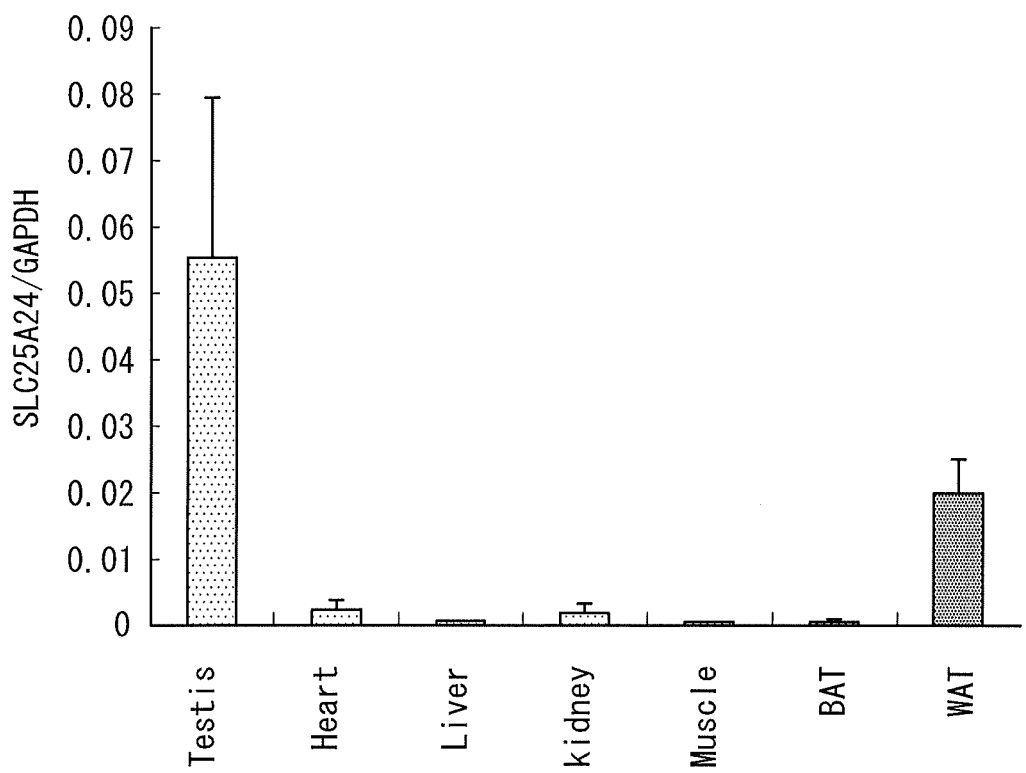
FIG. 2 is a graph showing the expression sites of the SLC25A24 gene.
Figure 3:
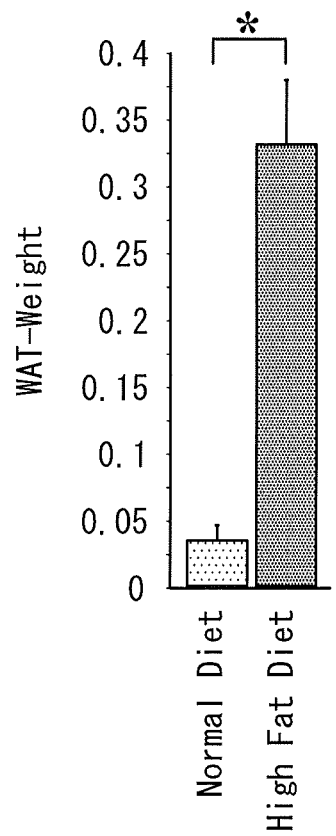
FIG. 3 includes a graph (a) showing a change in white adipose tissue by high fat diet and a graph (b) showing a change in expression of the SLC25A24 gene by high fat diet.
Figure 3:
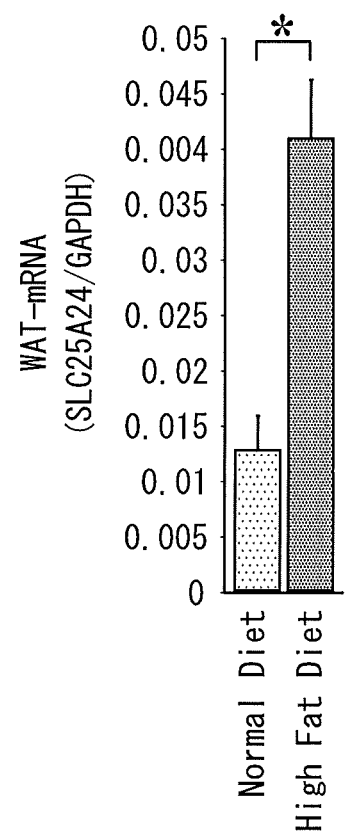

FIG. 2 is a graph showing the expression sites of the SLC25A24 gene. FIG. 3 includes a graph (a) showing a change in white adipose tissue by high fat diet and a graph (b) showing a change in expression of the SLC25A24 gene by high fat diet.

C57BL6 male mice (4 weeks old, n=6) were continuously fed with standard diet or high fat diet (High Fat Diet 32, CLEA Japan, Inc.) for 12 weeks. The mice were dissected at the end of 12 weeks from the start of feeding. The weights of the tissues were measured, and the SLC25A24 gene expression level in each tissue was measured by a real-time PCR method. White adipose tissue surrounding the kidney was collected and was subjected to RNA extraction after the measurement of the weight thereof.

The results were that the SLC25A24 gene expression was high in the white adipose tissue as shown in FIG. 2 and that, in the high fat diet group, the weight of white adipose tissue was significantly high as shown in FIG. 3(a) and the SLC25A24 gene expression at the mRNA level was significantly high as shown in FIG. 3(b).

Figure 4:
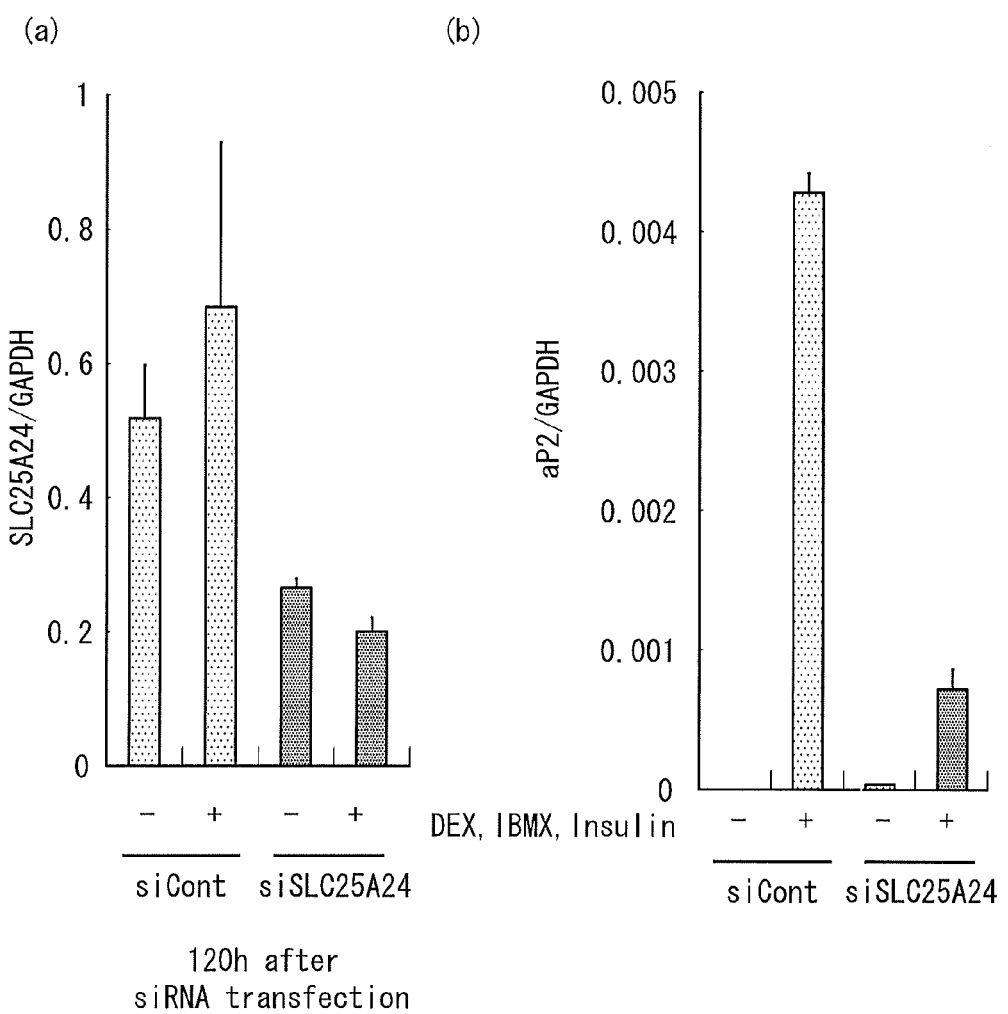
FIG. 4 includes a graph (a) showing a change in expression of SLC25A24 when the SLC25A24 gene was knocked out and a graph (b) showing a change in expression of an adipocyte differentiation marker, aP2, when the SLC25A24 gene was knocked out.

FIG. 4 includes a graph (a) showing a change in expression of SLC25A24 when the SLC25A24 gene was knocked out and a graph (b) showing a change in expression of an adipocyte differentiation marker, aP2, when the SLC25A24 gene was knocked out. In the figures, + and − respectively represent the presence and the absence of a differentiation-inducing stimulus. The expression was investigated by a real-time PCR method.

The SLC25A24 gene was knocked out using mouse adipocyte precursor 3T3L1 cells by siRNA (Dharmacon, siGENOME SMART pool, Cat No. M-054013-00) (control: Dharmacon, siCONTROL Non-Targeting siRNA No. 5, Cat No. D-001 210-05). The siRNA (5 nM) was transfected (Qiagen, HiPerFect) on the first day.

Differentiation induction was started on the following day of the transfection of the siRNA. The differentiation induction was started by culture in a medium prepared by adding 0.5 mM isobutylmethylxanthine (IBMX, Sigma), 1 μM dexamethasone (Dex, Sigma), and 10 μg/mL bovine insulin (Sigma) (MDI mixture) to a Dulbecco's modified Eagle's medium (DMEM) containing 10% FBS. The medium was replaced by the same fresh medium on the fourth day, and the RNA was collected on the fifth day.

The results were that the SLC25A24 expression was reduced by siSLC25A24 as shown in FIG. 4(a). On this occasion, in the control, the expression of the adipocyte differentiation marker, aP2, was induced by the differentiation-inducing stimulus as shown in FIG. 4(b), but the expression induction was significantly suppressed by siSLC25A24.

Figure 5:
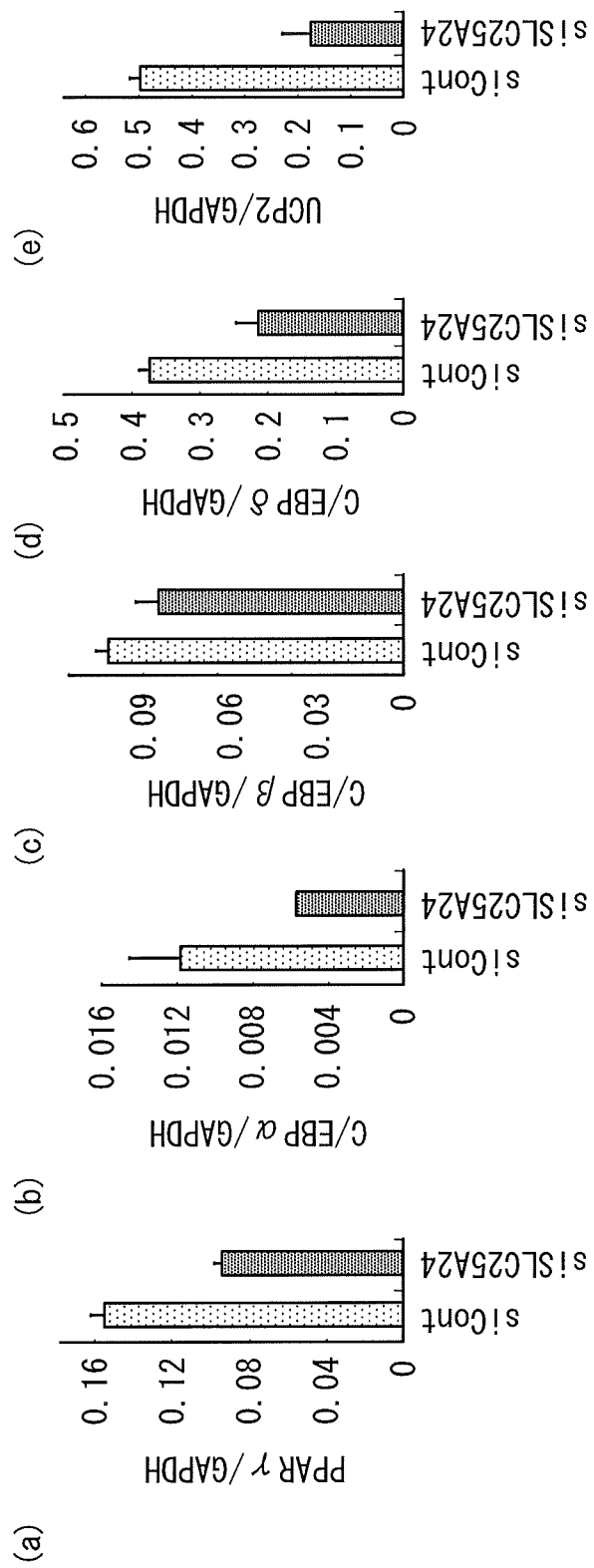
FIG. 5 includes a graph (a) showing a change in expression of an adipocyte differentiation marker, PPAR-$\gamma$, when the SLC25A24 gene was knocked out; a graph (b) showing a change in expression of a differentiation marker, C/EBP-$\alpha$, in the SLC25A24 gene knockout; a graph (c) showing a change in expression of a differentiation marker, C/EBP-$\beta$, in the SLC25A24 gene knockout; a graph (d) showing a change in expression of a differentiation marker, C/EBP-$\delta$, in the SLC25A24 gene knockout; and a graph (e) showing a change in expression of a differentiation marker, UCP2, in the SLC25A24 gene knockout.

Other adipocyte differentiation markers were also similarly investigated. FIG. 5 includes graphs (a) to (e) showing changes in expression of differentiation markers, PPAR-γ, C/EBP-α, C/EBP-β, C/EBP-δ, and UCP2, respectively.

As shown in FIG. 5, the expression of all differentiation markers was suppressed by siSLC25A24.

The differentiation marker aP2 is a fatty acid-binding protein of adipocytes and is expressed in adipocytes and macrophages and integrates inflammatory and metabolic responses. It was revealed by studies of aP2-deficient mice that this lipid chaperon plays an important role in pathological conditions of metabolic syndromes such as type 2 diabetes mellitus and arteriosclerosis. It is known that aP2 deficiency protects mice from insulin resistance in genetic or dietary obesity model mice.

The differentiation marker PPAR-γ is a peroxisome proliferating-agent responsive receptor that is expressed in the nuclei of most vertebrates and is a transcription factor group closely associated with intracellular metabolism of hydrocarbons, lipids, proteins, etc. and cell differentiation. PPAR-γ, a subtype of PPAR, is identified as a factor that binds to a fatty acid-specific enhancer of the aP2 gene. PPAR-γ is a transcription factor indispensable for adipocyte differentiation and energy storage and attracts attention as a target factor of a thiazolidine derivative serving as a drug for improving diabetes mellitus.

C/EBP is a bZIP protein having a basic amino acid region and a leucine zipper and constitutes a family composed of, for example, C/EBP-α, C/EBP-β, C/EBP-δ, C/EBP-1, and CHOP that are respectively encoded by different genes.

C/EBP-α is known to be associated with terminal differentiation of adipocytes and hepatocytes. In in vitro investigation using preadipocyte 3T3-L1 cells, C/EBP-β and C/EBP-δ are induced, and then they induce C/EBP-α and PPAR-γ. PPAR-γ is associated with adiposity, and C/EBP-α determines insulin sensitivity in adipocytes. Since their expression continues even in adipocytes, they are thought to be important for maintaining the shape and function of adipocytes. In contrast, the expression of C/EBP-β and C/EBP-δ decreases in adipocytes, and, therefore, they are thought to mainly function for inducing C/EBP-α and PPAR-γ in the early stage of differentiation and for inducing temporary cell proliferation.

UCP2 is an uncoupling protein and has a function of regulating thermogenesis in vivo. Activated UCP generates thermal energy for contributing to maintenance of body temperature. UCP includes several types: UCP1 exists in brown adipocytes, UCP2 is widely distributed all over the body, for example, in white adipocytes, skeletal muscle, the spleen, and the small intestine, UCP3 exists mainly in skeletal muscle, and UCP4 and UCP5 exist mainly in the brain.

Figure 6:
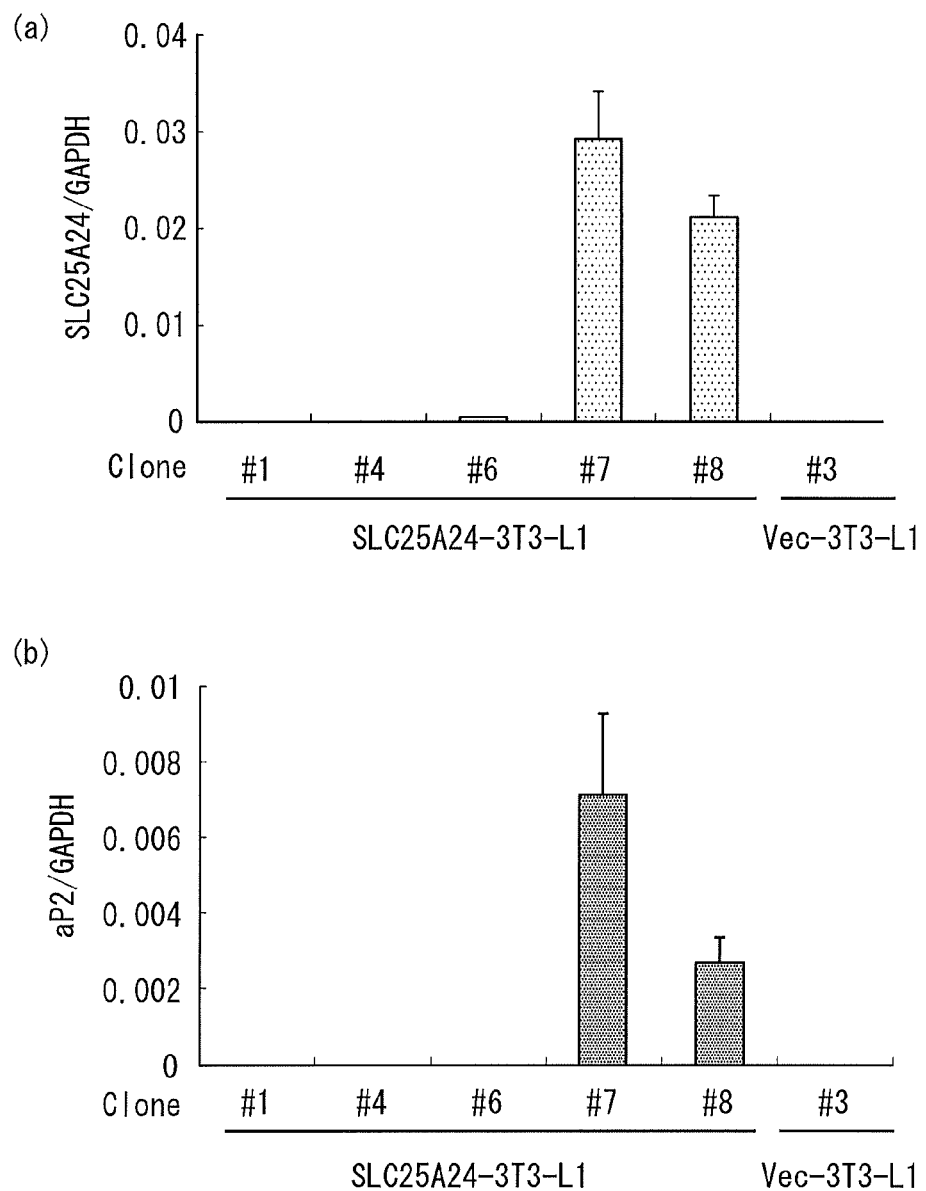
FIG. 6 includes a graph (a) showing a change in expression of SLC25A24 when the SLC25A24 gene was stably expressed and a graph (b) showing a change in expression of an adipocyte differentiation marker, aP2, when the SLC25A24 gene was stably expressed.

FIG. 6 includes a graph (a) showing a change in expression of SLC25A24 when the SLC25A24 gene was stably expressed and a graph (b) showing a change in expression of the adipocyte differentiation marker aP2 when the SLC25A24 gene was stably expressed.

Cells stably expressing SLC25A24 were established by transfecting mouse preadipocyte 3T3-L1 cells with a plasmid (pcDNA3-FLAG-SLC25A24) and performing selection with an antibiotic (G418).

As shown in FIG. 6(a), high expression of SLC25A24 was confirmed in clone Nos. 7 and 8 by a real-time PCR method, and as shown in FIG. 6(b), high expression of the differentiation marker aP2 was confirmed in these same cells. This revealed that differentiation of adipocytes was induced by stably expressing the SLC25A24 gene.

A SLC25A24 knockout mouse was produced in accordance with a usual method.

Figure 7:
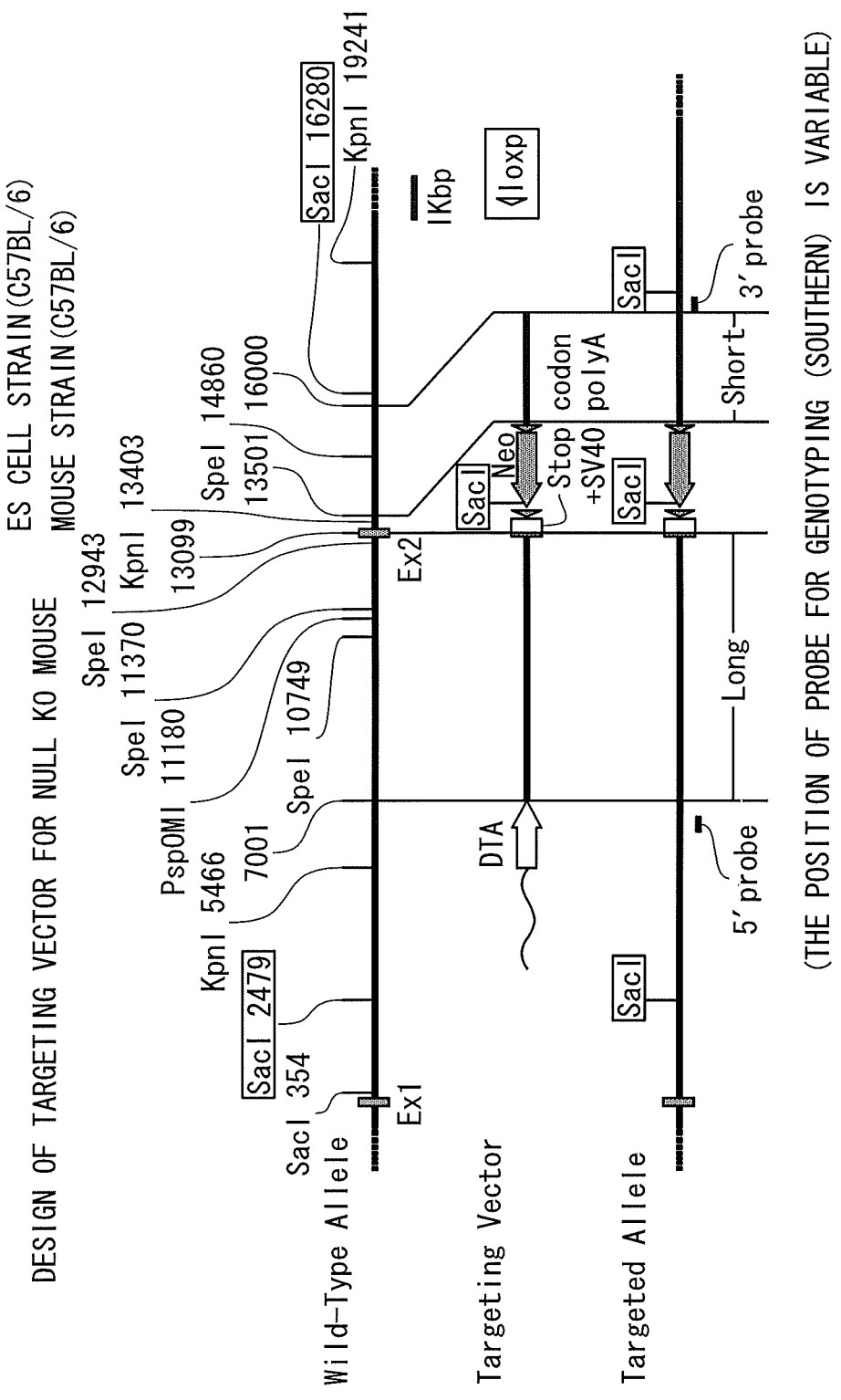
FIG. 7 is a design of a targeting vector for a knockout mouse.

FIG. 7 is a design of a targeting vector for a SLC25A24 knockout mouse.

This targeting vector was inserted into the SLC25A24 gene of mouse ES cells.

Figure 8:
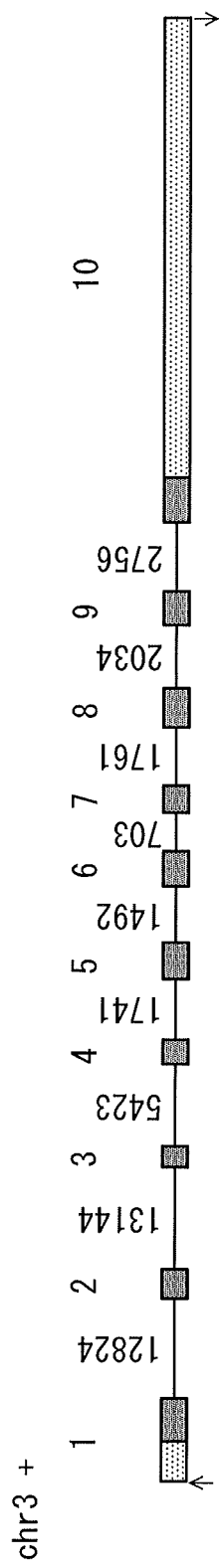
FIG. 8 is an explanatory drawing illustrating the structure of a mouse SLC25A24 gene.

FIG. 8 is an explanatory drawing illustrating the structure of a mouse SLC25A24 gene.

The mouse SLC25A24 gene is configured of ten exons. In the targeting vector used in this example for producing a knockout mouse, a sequence from the middle of exon 2 to the splice donor at the downstream position of exon 2 was removed whereas the splice acceptor at the upstream position of exon 2 of the mouse SLC25A24 gene was remained, and a stop codon and SV40 poly A were inserted at the region of the removed sequence.

Even if the promoter activity of this gene is strong so that downstream transcription is not terminated at the poly A site to cause mislead, the lack (127 bp) in exon 2 causes frameshift, which allows knockout of the gene. In addition, if trapping by the splice acceptor at the upstream position of exon 2 is possible, the transcription and the translation are terminated at the stop codon inserted at the downstream position of exon 2.

In the design of knockout mouse in this example, a predicted protein to be transcribed and translated is composed of 73 amino acids (about 8 kDa) and corresponds to the N-terminal site of the original sequence (NM_172685).

Figure 9:
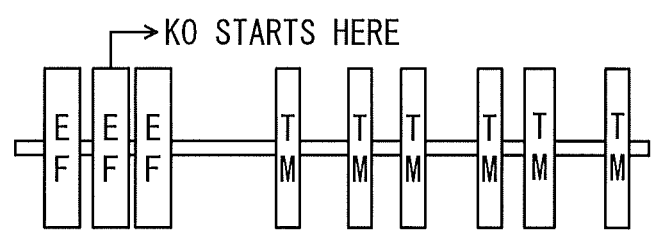
FIG. 9 is an explanatory drawing illustrating the structure of a mouse SLC25A24 protein.

FIG. 9 is an explanatory drawing illustrating the structure of a mouse SLC25A24 protein.

The SLC25A24 protein includes three EF-hand domains (EF) at the N-terminal and six transmembrane domains (TM) at the C-terminal. In the design of the knockout mouse in this example, a sequence starting from the middle of the second EF-hand domain is removed.

Figure 10:
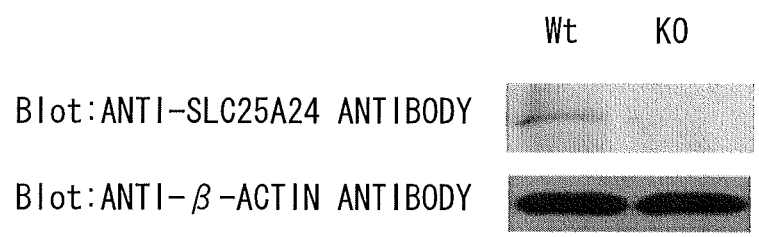
FIG. 10 shows the results (photographs) of Western blot for confirming a deficiency of the SLC25A24 protein in a knockout mouse.

FIG. 10 shows the results (photographs) of Western blot for confirming a deficiency of the SLC25A24 protein in a knockout mouse.

Whether or not the SLC25A24 protein was actually deleted in the SLC25A24 knockout mouse was investigated by a Western blot method.

Proteins were extracted from white adipose tissues of the wild-type (Wt) and SLC25A24 knockout (KO) mice and were subjected to Western blot using an anti-SLC25A24 antibody to confirm that the SLC25A24 protein was deleted in the white adipose tissue derived from the knockout mouse.

An anti-SLC25A24 antibody was produced as follows:
A rabbit was immunized with a synthetic peptide, as an antigen, prepared by adding cysteine to the C-terminal of a sequence from 146th to 161st of SLC25A24, EWRDYFLFN-PVTDIEE, which is an amino acid sequence common to human SLC25A24 and mouse SLC25A24, to obtain anti-human and mouse SLC25A24 polyclonal antibody.

As the method of preparing the antibody, a conventionally known method of producing antibody by immunization of a host animal can be appropriately used.

The type of the host animal for immunization is not particularly limited, and examples thereof include mammals such as rabbits, rats, mice, goats, sheep, horses, pigs, and guinea pigs and birds such as chickens, pigeons, ducks, and quails.

The administration route of the antigen is not particularly limited. For example, intracutaneous, subcutaneous, intraperitoneal, intravenous, or intramuscular administration can be appropriately employed.

A polyclonal antibody may be prepared by collecting body fluid of an immunized host animal, such as serum or ascites fluid, and isolating and purifying the antibody from the fluid.

A monoclonal antibody may be prepared by, for example, preparing hybridoma cells through fusion of myeloma cells and antibody-producing cells such as spleen cells or lymphoid cells of an immunized host animal, multiplying the hybridoma cells, and isolating and purifying hybridoma cells producing an antibody having specificity.

The method of purifying a polyclonal antibody or a monoclonal antibody is not particularly limited. For example, salting-out, dialysis, ion-exchange chromatography, affinity chromatography, or electrophoresis can be appropriately employed.

The method of screening antibody production is not particularly limited. For example, radioimmunoassay or enzyme immunoassay can be appropriately employed.

The thus-obtained antibody may be used for its own sake as an antibody, may be used as an active fragment of the antibody by being treated with, for example, an enzyme, or may be used as a reagent by being mixed with, for example, an agent.

Figure 11:
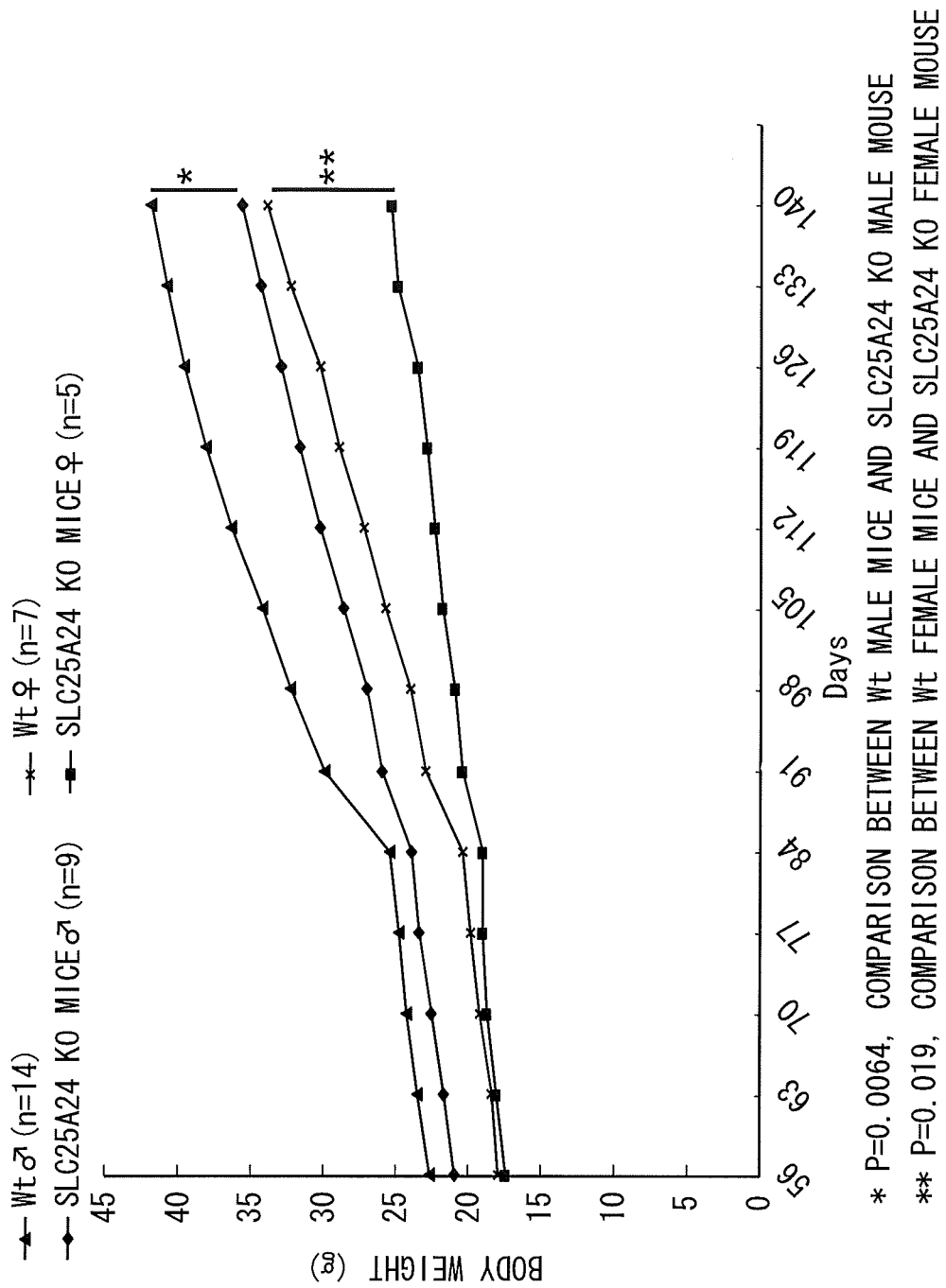
FIG. 11 is a graph showing changes in body weights of knockout mice by high fat diet.

FIG. 11 is a graph showing changes in body weights of knockout mice by high fat diet.

The strains of the SLC25A24 knockout mice obtained in the above were maintained, and the mice were loaded with high fat diet (trade name: HFD 32, manufactured by CLEA Japan, Inc., fat content: 32% by mass) from the age of 8 weeks. The body weights of two strains of the knockout mice and wild-type mice (C57BL/J) were compared.

The results were that the body weights of both male and female knockout mice were lower than those of the wild-type mice (male: P=0.0064, female: P=0.019).

Then, changes in genes in white adipose tissues of the knockout mice were searched through investigation by a microarray method.

Messenger RNAs were extracted from white adipose tissue derived from an SLC25A24 knockout mouse and white adipose tissue derived from a wild-type mouse. Using the mRNAs, expression analysis was conducted by a microarray method (GeneChip Mouse Gene 1.0 ST Array, Affymetrix, Inc.) in accordance with a usual method.

FIG. 12 is a list of genes that showed increased expression levels in knockout mice, and FIG. 13 is a list of genes that showed decreased expression levels in knockout mice.

As the genes showing increased expression levels, genes that showed ratios of the signal strengths in white adipose tissues derived from SLC25A24 knockout mice to those in white adipose tissues from the wild-type were 1.5 or more were listed. As the genes showing decreased expression levels, genes that showed ratios of the signal strengths in white adipose tissues derived from SLC25A24 knockout mice to those in white adipose tissues from the wild-type were 0.75 or less were listed.

In genes of higher ranks of the genes showing increased expression levels in the knockout mice, a plurality of genes associated with steroid metabolism (Hsd3b1, Cyp11b1, Cyp11a1, Srd5a2, Cyp21a1, Hsd3b6, and Star) is included.

SLC25A24 transgenic mice were produced in accordance with a usual method.

Figure 14:
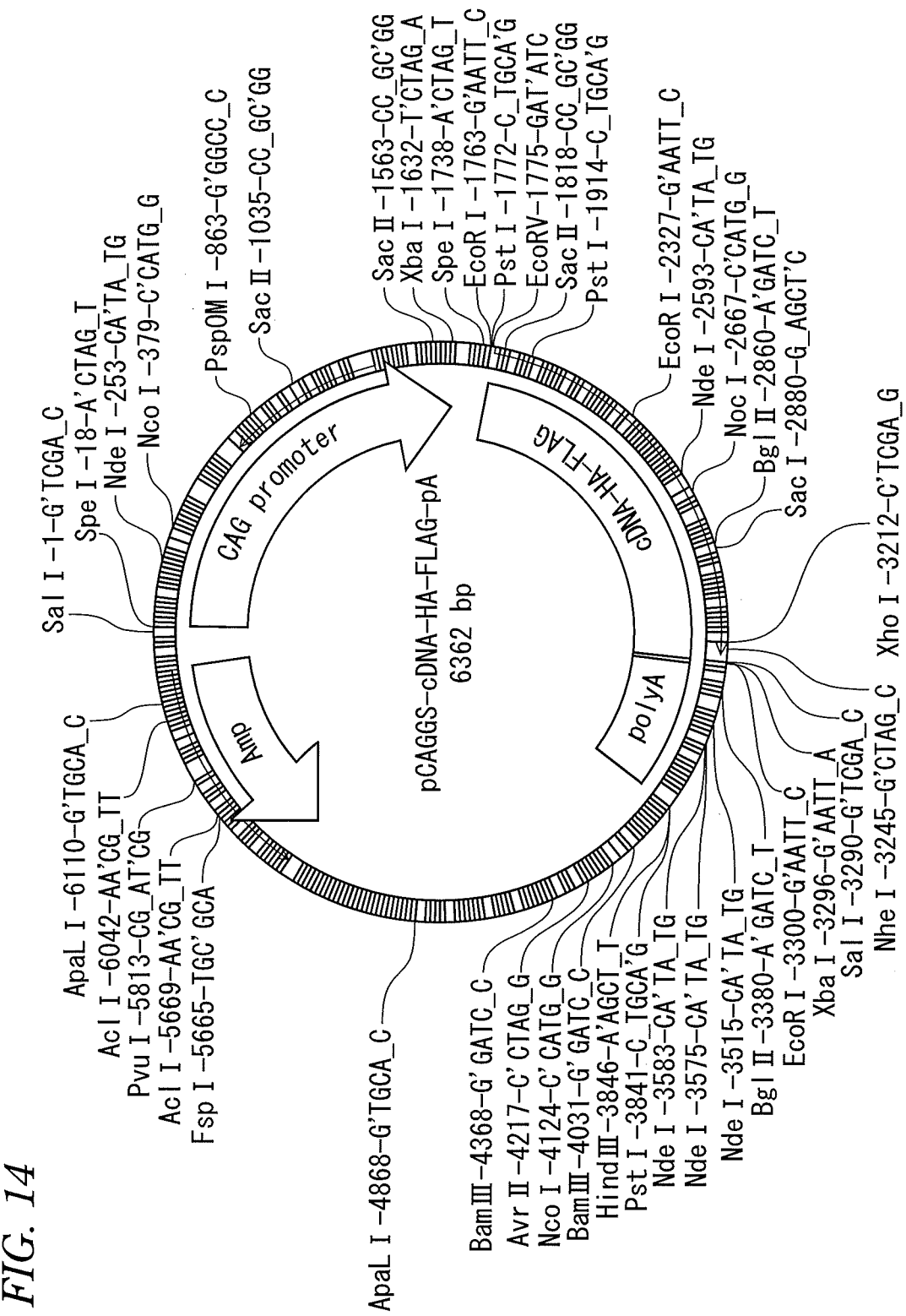
FIG. 14 is an explanatory drawing of a plasmid for producing a transgenic mouse.

FIG. 14 is an explanatory drawing of a plasmid (pCAGGS-SLC25A24-HA-FLAG-pA) for producing a transgenic mouse.

A plasmid (pCAGGS-SLC25A24-HA-FLAG-pA) was produced by inserting the isolated human SLC25A24 gene into a pCAGGS vector and adding an HA-FLAG tag to the C-terminal.

The pCAGGS vector allows a gene that is desired to be introduced to overexpress in almost all over the body by using a CAG promoter, that is, a structure in which a cytomegalovirus enhancer and a chicken β-actin promoter are linked, and a poly A signal site of a rabbit β-globin gene. SLC25A24 transgenic mice that highly express the SLC25A24 gene in all over the body (background: C57BL/J) were produced in accordance with a usual method using the produced plasmid.

Figure 15:
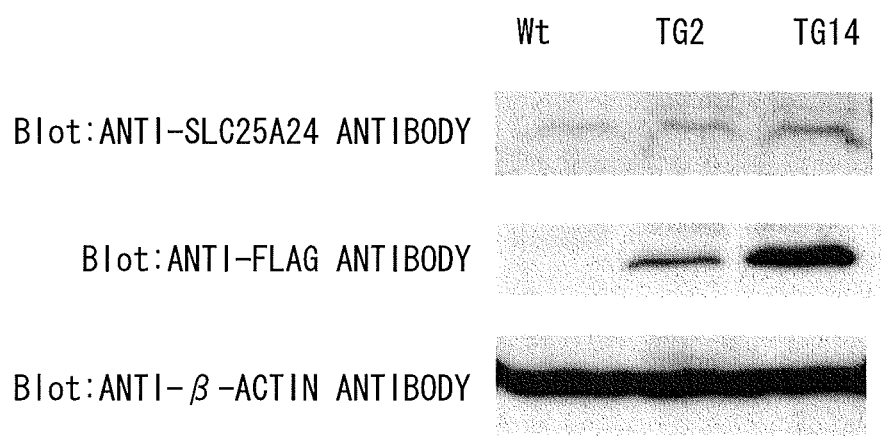
FIG. 15 shows the results (photographs) of Western blot for confirming high expression of the SLC25A24 protein in transgenic mice.

FIG. 15 shows the results (photographs) of Western blot for confirming high expression of the SLC25A24 protein in the transgenic mice.

Whether or not the SLC25A24 transgenic mice actually highly express the SLC25A24 protein was investigated by a Western blot method.

Proteins were extracted from white adipose tissues of wild-type (Wt) and two strains of transgenic mice (TG2: line 2, TG14: line 14) and were subjected to Western blot using an anti-SLC25A24 antibody.

The results confirmed that the expression of the SLC25A24 protein in the two strains of the transgenic mice was higher than that in the wild-type mouse. Since the induced SLC25A24 gene is provided with a FLAG tag, the expression of the induced SLC25A24 gene can be also detected using an anti-FLAG antibody.

Figure 16:
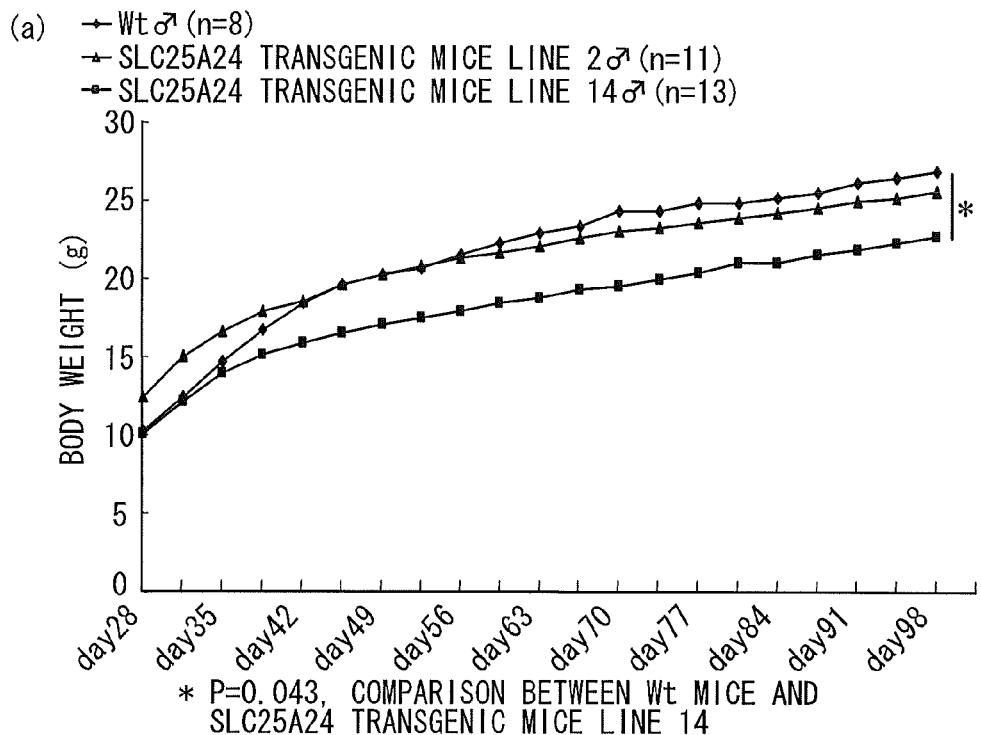
FIG. 16 includes a graph (a) showing changes in body weights of male transgenic mice by high fat diet and a graph (b) showing changes in body weights of female transgenic mice by high fat diet.
Figure 16:
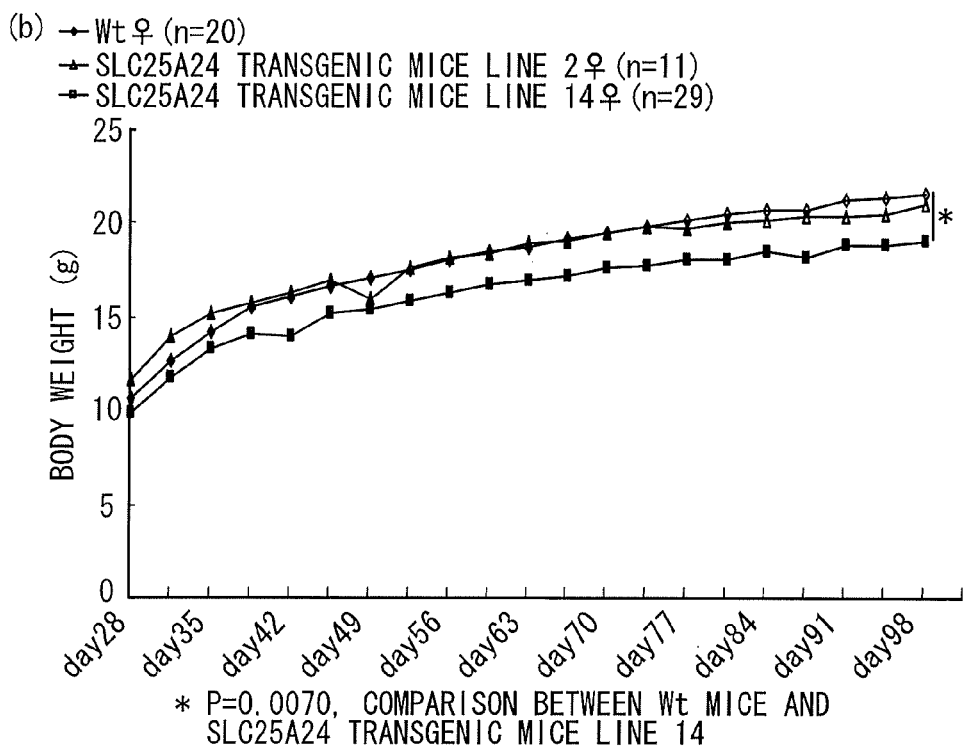
Figure 16:
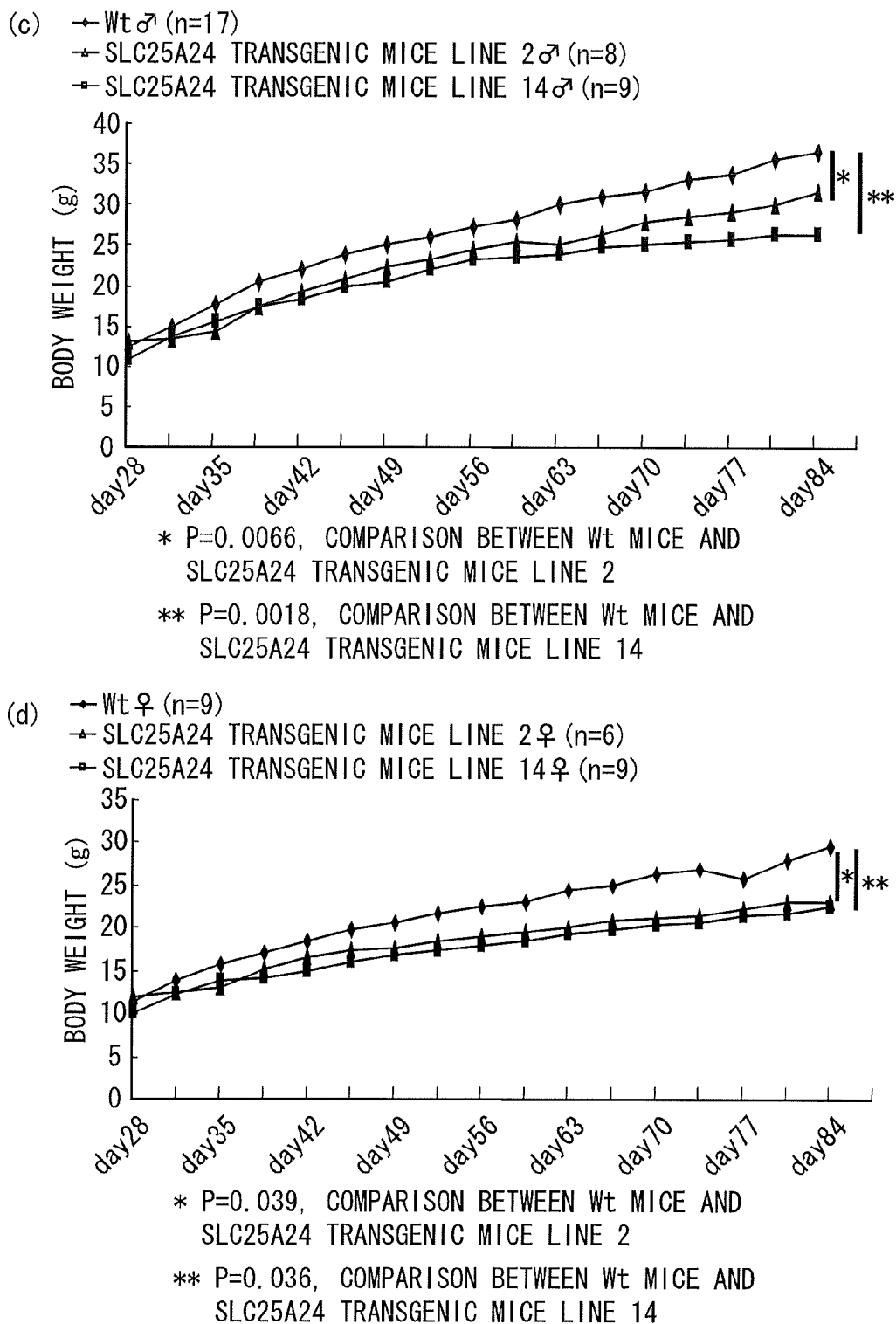

FIG. 16 shows changes in body weights of transgenic mice by high fat diet and includes a graph (a) showing the results in high fat diet male mice and a graph (b) showing the results in high fat diet female mice.

Two strains (line 2 and line 14) of the SLC25A24 transgenic mice obtained in the above were maintained, and the mice were loaded with high fat diet (trade name: HFD 32, manufactured by CLEA Japan, Inc., fat content: 32% by mass) from the age of 4 weeks. The body weights of two strains of the knockout mice and wild-type mice (C57BL/J) were compared.

The results were that the body weights of both male and female knockout mice were significantly lower than those of the wild-type mice (high fat diet male, line 2: P=0.0066, line 14: P=0.0018; and high fat diet female, line 2: P=0.039, line 14: P=0.036).

Thus, it was revealed that a change in expression level of SLC25A24 directly affects the body weight.

As described above, it was recognized that an anti-obesity drug having an effect of suppressing differentiation of adipocytes can be obtained by using an agent that suppresses or regulates the expression of the SLC25A24 gene or inhibits or regulates the activity thereof. The anti-obesity drug according to the present invention is useful as a medicine for improving obesity such as adipositas.

The anti-obesity drug is not necessarily required to suppress the expression of the SLC25A24 gene or inhibit the activity thereof as long as the drug has an effect of regulating the expression or the activity to suppress differentiation of adipocytes as a result.

The ortholog of SLC25A24 is not particularly limited. For example, those derived from non-human animals such as mammals, e.g., mice, rats, hamsters, guinea pigs, rabbits, cattle, sheep, pigs, goats, and monkeys, can be targets.

The SLC25A24 as the target may have one or more variations in the amino acid sequence encoded thereby as long as it has differentiation potency of adipocytes.

The anti-obesity drug according to the present invention may appropriately contain a pharmaceutically acceptable carrier.

Examples of the carrier include excipients such as sucrose, starch, mannite, sorbit, lactose, glucose, cellulose, talc, calcium phosphate, and calcium carbonate; binders such as cellulose, methyl cellulose, hydroxypropyl cellulose, polypropyl pyrrolidone, gelatin, gum arabic, polyethylene glycol, sucrose, and starch; disintegrators such as starch, carboxymethyl cellulose, hydroxypropyl starch, sodium glycol starch, sodium bicarbonate, calcium phosphate, and calcium citrate; lubricants such as magnesium stearate, aerosil, talc, and sodium lauryl sulfate; aromatics such as citric acid, menthol, glycyrrhizin ammonium salt, glycine, and orange powder; preservatives such as sodium benzoate, sodium hydrogen sulfite, methylparaben, and propylparaben; stabilizers such as citric acid, sodium citrate, and acetic acid; suspensions such as methyl cellulose, polyvinyl pyrrolidone, and aluminum stearate; dispersants such as surfactants; diluents such as water, physiological saline, and apple juice; and base waxes such as cacao butter, polyethylene glycol, and kerosene.

Examples of formulation suitable for oral administration of the anti-obesity drug include a liquid drug in which an effective dose of a substance is dissolved in a diluent such as water or physiological saline; a capsule, a sachet, or a tablet in which an effective dose of a substance is included as a solid or granules; a suspension drug in which an effective dose of a substance is suspended in an appropriate dispersant; an emulsion drug in which a solution of an effective dose of a substance is dispersed and emulsified in an appropriate dispersant; and powder and granules.

Examples of formulation suitable for parenteral administration such as intravenous injection, subcutaneous injection, intramuscular injection, and local injection include aqueous and nonaqueous isotonic sterile injectable solutions optionally containing antioxidants, buffers, bacteriostatics, tonicity agents, and other ingredients; and aqueous and nonaqueous sterile suspension drugs optionally containing suspensions, solubilizers, thickeners, stabilizers, preservatives, and other ingredients.

Such a pharmaceutical preparation may be enclosed in a container such as an ampule or vial so as to contain a unit dose or a multiple dose. Alternatively, an active ingredient and a pharmaceutically acceptable carrier may be lyophilized and stored in a state allowing them to be dissolved or suspended in an appropriate sterile vehicle just before use.

The dose of the anti-obesity drug varies depending on, for example, the activity and the type of an active ingredient, administration route, the degree of seriousness of a disease, animal species as a subject to be administered, and drug receptivity, body weight, and age of a subject to be administered, but a dose of about 0.001 mg to about 5.0 g/kg/day is a standard for an adult.

The screening of the anti-obesity drug includes the step of evaluating whether or not each test substance can suppress or regulate the expression of the SLC25A24 gene or can inhibit or regulate the activity thereof; and the step of selecting a test substance that can suppress or regulate the expression of the SLC25A24 gene or can inhibit or regulate the activity thereof and thereby prevents or treats obesity or an obesity-related condition or disease, as an active substance for preventing or treating obesity or an obesity-related condition or disease.

In the step of evaluation, any known compounds and novel compounds can be used as the test substances to be subjected to the screening method. Examples of the test substances include organic low-molecular compounds, compound libraries produced by combinatorial chemistry technology, nucleic acids (e.g., nucleosides, oligonucleotides, and polynucleotides), carbohydrates (e.g., monosaccharides, disaccharides, oligosaccharides, and polysaccharides), lipids (e.g., saturated or unsaturated straight, branched, and ring-containing fatty acids), amino acids, proteins (e.g., oligopeptides and polypeptides), random peptide libraries produced by solid synthesis or a phage display method, and natural ingredients derived from, for example, bacteria, animals, plants, and marine organisms.

The step of evaluation can employ any method that can evaluate the effects of suppressing or regulating the expression of SLC25A24 or inhibiting or regulating the activity thereof due to test substances. For example, a non-human animal or cells that allow measurement of suppression or regulation of SLC25A24 expression or inhibition or regulation of the activity thereof may be used.

Examples of the non-human animal include mammals such as mice, rats, hamsters, guinea pigs, rabbits, dogs, and monkeys. Model animals showing obesity or an obesity-related condition or disease also may be used.

Examples of the model animals showing obesity or an obesity-related condition or disease include model animals in a state of obesity or obesity-related disease (e.g., ob/ob mice, Ay mice, Zucker-fatty rats, Otsuka long-evans fatty (OLETF) rats, and overeating mice and rats induced by administration of a drug such as glutamic acid); examples of the model animals showing an obesity-related condition or disease include model animals loaded with high fat diet and model animals of diseases caused by abnormal glucose tolerance (e.g., db/db mice, KKAy mice, Wistar-fatty rats, Goto-Kakizaki (GK) rats, Otsuka long-evans fatty (OLETF) rats, Akita mice, and pancreas destruction mice and rats due to administration of a drug such as streptozotocin), model animals of hypoadiponectinemia (e.g., adiponectin-deficient mice, ob/ob mice, and A-ZIP lipodystrophic mice), model animals of hyperinsulinemia (e.g., IRS1-deficient mice), model animals of arteriosclerosis (e.g., apo E-deficient mice, LDL receptor-deficient mice, and WHHL rabbits), and model animals of hypertension (e.g., 11β-HSD-induced mice, SHR rats, and SHRSP rats).

In the case of using a non-human animal, a test substance may be administered by any conventionally known method to the non-human animal. Examples of the administration route include oral administration and parenteral administration (e.g., intravenous injection, subcutaneous injection, intraperitoneal injection, and local injection). The dose, administration intervals, administration period, and other factors are appropriately determined depending on the test substance and the type of the animal.

In the measurement of the degree of obesity of a non-human animal, not only the body fat mass but also the body fat percentage, body weight, basal metabolism, and other factors can be used as indices.

Whether or not a test substance has an effect of suppressing the expression of SLC25A24 may be evaluated by measuring the expression level of SLC25A24 in an animal administered with the test substance.

The expression level may be measured by, for example, collecting a biological specimen such as adipose tissue from a non-human animal and measuring the transcription product in the specimen.

The screening may be performed using tissues or cells of a non-human animal, such as, adipose tissues or adipocytes.

Cells allowing direct evaluation of the expression level of an SLC25A24 product are SLC25A24-expressing cells such as adipocytes, and cells allowing indirect evaluation of the expression level of an SLC25A24 product are cells enabling of reporter assay for a transcriptional regulatory region of the SLC25A24 gene.

The cells enabling of reporter assay for a transcriptional regulatory region of the SLC25A24 gene are cells containing an SLC25A24 gene transcriptional regulatory region and a reporter gene linked to the region in a workable manner.

The transcriptional regulatory region of the SLC25A24 gene may be any region that can suppress the expression of SLC25A24, and examples thereof include a region having a capability of suppressing transcription and composed of a base sequence of the transcriptional regulatory region of the SLC25A24 gene having deletion, substitution, or addition of one or more bases therein.

The present invention also can provide a non-human animal having a deficiency in the SLC25A24 gene and tissues or cells derived from the animal.

The non-human animal can be a model animal in an anti-obesity, low insulin, or low leptin state and has a significant difference compared with the wild-type.

The tissues or cells derived from the animal are useful for, for example, the screening according to the present invention, screening of a marker gene of a disease or condition that requires improvement of obesity, screening of an adipocyte marker gene, and analysis of a pathological mechanism of a disease or condition that requires improvement of obesity. These can be achieved by expression profile analysis measuring the expression profile in a non-human animal according to the present invention with, for example, a microarray or a protein chip and comparing the expression profile with that of a control animal.

INDUSTRIAL APPLICABILITY

The method or kit for evaluating a predisposition to obesity according to the present invention effectively evaluates whether or not a subject has a predisposition to obesity or an obesity-related condition or disease and therefore contributes to prevention and early treatment of various diseases associated with obesity. In addition, the anti-obesity drug according to the present invention suppresses differentiation of adipocytes and therefore contributes to treatment of various diseases associated with obesity without causing unfavorable other effects. Thus, the present invention is effective as countermeasures against obesity, which is being recognized as a social problem, and accordingly has a high industrial utility value.

The invention claimed is:
1. A method for diagnosing susceptibility to increased body fat after menopause in a female subject, the method comprising:
    collecting gDNA from the subject;
    measuring the copy number of the sequence of 108534690-108535300 on chromosome 1 from intron 1 of SLC25A24 gene in the gDNA of the subject, wherein the sequence is measured by a TaqMan PCR method;
    detecting a copy number of zero for the sequence of 108534690-108535300 on chromosome 1 from intron 1 of SLC25A24 gene in the subject; and
    diagnosing the subject with a zero copy number of the sequence as more susceptible to increased body fat after menopause compared to female subjects having one or more copy number(s) of the sequence.

* * * * *